United States Patent [19]

Nabi et al.

[11] Patent Number: 5,334,375
[45] Date of Patent: Aug. 2, 1994

[54] ANTIBACTERIAL ANTIPLAQUE ORAL COMPOSITION

[75] Inventors: Nuran Nabi, North Brunswick; Michael Prencipe, East Windsor; Abdul Gaffar, Princeton, all of N.J.

[73] Assignee: Colgate Palmolive Company, Piscataway, N.J.

[21] Appl. No.: 914,083

[22] Filed: Jul. 16, 1992

Related U.S. Application Data

[63] Continuation-in-part of Ser. No. 738,766, Aug. 1, 1991, Pat. No. 5,202,112, Ser. No. 655,571, Feb. 14, 1991, Pat. No. 5,178,851, Ser. No. 657,885, Feb. 19, 1991, Pat. No. 5,180,578, Ser. No. 754,887, Sep. 6, 1991, Pat. No. 5,192,530, and Ser. No. 758,345, Sep. 9, 1991, Pat. No. 5,192,531, which is a continuation of Ser. No. 399,669, Aug. 25, 1989, abandoned, and Ser. No. 398,592, Aug. 28, 1989, Pat. No. 5,188,821, said Ser. No. 655,571, is a continuation of Ser. No. 398,566, Aug. 25, 1989, Pat. No. 5,032,386, said Ser. No. 657,885, is a continuation of Ser. No. 398,605, Aug. 25, 1989, abandoned, said Ser. No. 754,887, is a continuation of Ser. No. 398,606, Aug. 25, 1989, abandoned, said Ser. No. 398,566, Ser. No. 398,605, Ser. No. 398,606, Ser. No. 399,669, and Ser. No. 398,592, each is a continuation-in-part of Ser. No. 291,712, Dec. 29, 1988, Pat. No. 4,894,220, and Ser. No. 346,258, May 1, 1989, Pat. No. 5,043,154, which is a continuation of Ser. No. 8,901, Jan. 30, 1987, abandoned.

[51] Int. Cl.⁵ .......................... A61K 7/16; A61K 7/18
[52] U.S. Cl. ...................... 424/52; 424/49; 424/57
[58] Field of Search ...................... 424/49–58

[56] References Cited

U.S. PATENT DOCUMENTS

| | | | |
|---|---|---|---|
| 3,429,963 | 2/1969 | Shedlovsky | 424/56 |
| 3,629,477 | 12/1971 | Model et al. | 514/520 |
| 4,022,880 | 5/1977 | Vinson et al. | 424/54 |
| 4,806,342 | 2/1989 | Gaffar et al. | 424/52 |
| 4,808,400 | 2/1989 | Gaffar et al. | 424/52 |
| 4,808,401 | 2/1989 | Gaffar et al. | 424/52 |
| 4,889,712 | 12/1989 | Gaffar et al. | 424/52 |
| 4,894,220 | 1/1990 | Nabi et al. | 424/52 |
| 4,921,692 | 5/1990 | Gaffar et al. | 424/52 |
| 4,921,693 | 5/1990 | Gaffar et al. | 424/52 |
| 4,980,153 | 12/1990 | Jackson et al. | 424/52 |
| 5,017,362 | 5/1991 | Gaffar et al. | 424/52 |
| 5,032,385 | 7/1991 | Reed et al. | 424/49 |
| 5,034,488 | 7/1991 | Tazi et al. | 526/271 |
| 5,037,635 | 8/1991 | Nabi et al. | 424/52 |
| 5,037,637 | 8/1991 | Gaffar et al. | 424/52 |
| 5,043,154 | 8/1991 | Gaffar et al. | 424/52 |
| 5,080,887 | 1/1992 | Gaffar et al. | 424/52 |
| 5,135,738 | 8/1992 | Gaffar et al. | 424/52 |
| 5,139,769 | 8/1992 | Gaffar et al. | 424/52 |
| 5,156,835 | 10/1992 | Nabi et al. | 424/52 |
| 5,167,951 | 12/1992 | Gaffar et al. | 424/52 |
| 5,180,578 | 1/1993 | Gaffar et al. | 424/52 |
| 5,202,112 | 4/1993 | Prencipe et al. | 424/52 |

Primary Examiner—Shep K. Rose
Attorney, Agent, or Firm—Robert L. Stone; Murray M. Grill; Robert C. Sullivan

[57] ABSTRACT

An oral composition containing a substantially water insoluble noncationic antibacterial antiplaque agent such as triclosan and a synthetic cross-linked polymer such as cross-linked poly (methylvinyl ether/maleic acid or anhydride) as antibacterial-enhancing agent to enhance delivery of said antibacterial agent to, and the retention thereof on, oral surfaces, and a method of promoting oral hygiene therewith.

33 Claims, No Drawings

ANTIBACTERIAL ANTIPLAQUE ORAL COMPOSITION

This application is a continuation-in-part (CIP) of application Ser. No. 07/738,766 filed Aug. 1, 1991 and now U.S. Pat. No. 5,202,112 of U.S. application Ser. No. 07/655,571 filed Feb. 14, 1991 as a continuation (CON) of Ser. No. 07/398,566, filed Aug. 25, 1989, and now U.S. Pat. No. 5,032,386, of 07/657,885, filed Feb. 19, 1991 (now U.S. Pat. No. 5,180,578) as a CON of abandoned Ser. No. 07/398,605, of Ser. No. 07/754,887 filed Sep. 6, 1991 (now U.S. Pat. No. 5,192,530) as a CON of abandoned Ser. No. 07/398,606, and of Ser. No. 758,345 filed Sep. 9, 1991 (now U.S. Pat. No. 5,192,531) as a CON of abandoned Ser. No. 07/399,669, all said abandoned applications having been filed Aug. 25, 1989, and of Ser. No. 07/398,592 filed Aug. 28, 1989 (now U.S. Pat. No. 5,188,821), which latter application, like said abandoned applications, is or were CIP's of Ser. No. 07/291,712 filed Dec. 29, 1988 and now U.S. Pat. No. 4,894,220, and of application Ser. No. 346,258 filed May 1, 1989 (now U.S. Pat. No. 5,043,154) as a CON of abandoned Ser. No. 07/008991 filed Jan. 30, 1987, all commonly assigned and the disclosures of which are incorporated herein.

This invention relates to an antibacterial antiplaque oral composition. More particularly, it relates to an oral composition containing a substantially water-insoluble noncationic antibacterial agent (NAA) effective to inhibit plaque, and a cross-linked polymer as an antibacterial-enhancing agent (AEA) which enhances the antibacterial antiplaque activity of the NAA.

Dental plaque is a soft deposit which forms on teeth as opposed to calculus which is a hard calcified deposit on teeth. Unlike calculus, plaque may form on any part of the tooth and soft oral tissue surface, especially at the gingival margin. Hence, beside being unsightly, it is implicated in the occurrence of gingivitis.

Accordingly, it is highly desirable and an object of this invention, to include in oral compositions antibacterial agents which have been know to reduce plaque, especially substantially water-insoluble noncationic antibacterial agents such as triclosan (2,4,4'trichloro-2'-hydroxydiphenyl ether). In U.S. Pat. No. 4,022,880 to Vinson et al, a compound providing zinc ions as an anticalculus agent is admixed with an antibacterial agent, a wide variety of which are described, including noncationic compounds such as halogenated salicylanilides and halogenated hydroxydiphenyl ethers. The noncationic antibacterial antiplaque halogenated hydroxydiphenyl ether, triclosan, has been described in many publications, including its combination with zinc citrate trihydrate in European Patent (EP) Publication 0161,899 to Saxton et al. Triclosan is also disclosed in EP Publication 0271,332 to Davis as a toothpaste component containing a solubilizing agent such as propylene glycol. German Patent Disclosure DE 3,532,860 describes triclosan in combination with a copper compound. EP Publication 0278, 744 discloses triclosan combined with a potassium-containing tooth desensitizing agent. EP 0161,898 discloses it as an antiplaque agent in a dentifrice formulated to contain a lamellar liquid crystal surfactant phase.

In several of the aforementioned commonly assigned patent applications, it is shown that the antiplaque effectiveness of NAA's such as triclosan in oral compositions is greatly enhanced by including in such compositions an AEA which enhances the delivery of said NAA's to, and retention thereof on, oral surfaces.

In the aforementioned commonly assigned patent application No. 07/738,766 (U.S. Pat. No. 5,202,112) toothpaste and dental gel compositions are described containing an amount of a synthetic linear viscoelastic cross-linked polymeric thickening agent, especially a cross-linked methyl vinyl ether/maleic anhydride copolymer, effective to render the composition linearly viscoelastic, and a method of promoting oral hygiene by applying an effective amount of the composition to dental surfaces.

The present invention is at least in part based on our discovery that the antiplaque effectiveness of NAA's such as triclosan in oral compositions is still further enhance by including in such compositions as an AEWA one or a mixture of said synthetic linear viscoelastic cross-linked polymeric agents, such inclusion in dentifrices such as toothpaste and dental gel compositions further rendering such compositions desirably linearly viscoelastic.

In accordance with certain of its aspects, the present invention relates to an oral composition comprising in an orally acceptable vehicle an effective antiplaque amount of a substantially water-insoluble noncationic antibacterial agent and an antibacterial-enhancing agent in an amount effective to enhance delivery of said antibacterial agent to, and the retention thereof on, oral surfaces, said antibacterial-enhancing agent comprising a synthetic cross-linked polymer having in a 1 wt. % aqueous solution an elastic or storage modulus $G'$ and a viscous or loss modulus $G''$ substantially independent of frequency in an applied frequency range of 0.1 to 100 radians/sec., a $G'$ minimum value of 5,000 dynes/sq. cm which varies less than 1 order of magnitude of its original value, and a ratio of $G''/G'$ ranging from more than 0.05 to less than 1.

The invention further includes a method for promoting oral hygiene and inhibiting plaque by applying to dental surfaces including teeth, preferably in the oral cavity, an effective amount of the compositions of this invention. According to further aspects of the present invention, the aforesaid composition preferably further contains an effective anticalculus amount of material comprising at least one substantially water soluble synthetic linear molecularly dehydrated polyphosphate salt such as tetrasodium pyrophosphate (TSPP) or tetrapotassium pyrophosphate (TKPP) or a mixture thereof, and/or an amount of a fluoride ion source effective to supply about 25 ppm to about 5,000 ppmm of fluoride ions.

All the substantially water insoluble NAA's in the above identified predecessor patent applications are non-exclusively operative herein. The NAA, or any mixture thereof, is present in the oral composition in an effective antiplaque amount, typically about 0.01%–5% by weight, preferably about 0 03%–1% more preferably about 0 25 0.5% or about 0.25% to less than 0.5% and most preferably about 0.25–0.35% e.g. about 0.3% in a dentifrice (toothpaste, dental gel, etc.) or preferably about 0.03–0.3% by weight, most preferably about 0.03–0.1% in a mouthwash or liquid dentifrice. The NAA is substantially water-insoluble, meaning that its solubility is less than about 1% by weight in water at 25° C. and may be even less than about 0.1%.

The halogenated diphenyl ethers are most preferred, especially triclosan. Also preferred are the phenolic compounds phenol, thymol, eugenol, hexyl resorcinol and 2,2' methylene bis (4-chloro-6-bromophenol).

All the synthetic linear viscoelastic cross-linked polymers disclosed in the above identified predecessor patent application Ser. No. 07/738,766 (U.S. Pat. No. 5,202,112) are non-exclusively operative herein as AEA's containing at least one and preferably a plurality of delivery-enhancing groups, preferably acidic such as sulfonic or phosphinic or more preferably phosphonic or carboxylic, or salt thereof, and at least one and preferably a plurality of retention-enhancing cross-linking, preferably organic, groups. The delivery-enhancing group refers to one which attaches or substantively, adhesively, cohesively or by physical entrapment bonds the cross-linked AEA (carrying the antibacterial agent) to oral (e.g. tooth and gum) surfaces, thereby delivering the antibacterial agent to such surfaces. The retention-enhancing group, ordinarily organic and hydrophobic attaches or otherwise bonds the antibacterial agent to the cross-linked AEA, thereby promoting retention of the antibacterial agent to the cross-linked AEA and indirectly to the oral surfaces. The retention-enhancing cross-linking groups in the cross-linked polymers employed herein provide increased sites for physical and chemical entrapment of the antibacterial agent. The presence of a higher molecular weight, more hydrophobic cross-linking moiety in the cross-linked polymer still further promotes such physical entrapment.

Still further retention-enhancement is provided when the cross-linked AEA, preferably an anionic cross-linked polymer comprising a chain or backbone with repeating units each preferably containing at least one carbon atom also contains at least one and preferably a plurality of directly or indirectly pendant monovalent retention-enhancing groups geminally, vicinally or otherwise bonded to atoms, preferably carbon, in the chain. as in the preferred cross-linked copolymers of maleic acid or anhydride with another ethylinically unsaturated monomer such as methyl vinyl ether and of polymers containing units from styrene phosphonic acid. It has been found, for example, that the degree of delivery and retention of triclosan on oral surfaces achieved with oral compositions containing triclosan and 2% of maleic acid or anhydride/methyl vinyl ether copolymer is significantly surpassed with oral compositions containing triclosan and as little as 0.1% of the same copolymer but cross-linked according to the invention. The cross-linked AEA's are employed herein generally in amounts of about 0.02% to about 3%, preferably about 0.05% to about 1%, more preferably about 0.1% to about 0.5%.

Linearly viscoelastic dentifrice compositions according to the invention have excellent stability against phase separation or syneresis, viscosity change in storage, and settling of dissolved, dispersed or suspended particles under high and low temperature conditions, freedom from fish eyes, excellent texture and other cosmetic properties, ease of extrusion from a dispensing tube, pump or the like (easily shear thinned), good stand-up after extrusion (quick recovery of structure), and improved fluoride ion availability to dental enamel leading to improved anti-caries effects.

These dentifrice compositions will retain sufficient energy when a stress or strain is applied, at least over the extent expected to be encountered for products of this type, for example, when squeezed out of a toothpaste tube or pump to return to its previous condition and exhibit excellent stand-up when the stress or strain is removed. The compositions therefore will also have a high cohesive property, namely, when a shear or strain is applied to a portion of the compositions to cause it to flow, the surrounding portions will follow. As a result of this cohesiveness of the linear viscoelastic characteristic, the compositions will readily flow uniformly and homogeneously from a pump or tube when it is squeezed thereby contributing to the stand-up and ease of extrusion properties which characterize the compositions of this invention. The linear viscoelastic property also contributes to improved physical stability against phase separation of suspended particles by providing a resistance to movement of the particles due to the strain exerted by a particle on the surrounding medium.

The above-described linear viscoelastic properties of the dentifrice compositions of this invention are fundamentally provided by the defined synthetic linearly viscoelastic cross-linked polymeric thickening agents which generally have a molecular weight (M. W.) of about 1,000 to about 5,000,000. The homopolymers and copolymers (from 2, 3 or more monomers) to be cross-linked are generally anionic comprising a chain or backbone containing repeating units each preferably containing at least one carbon atom (typically only carbon atoms in the chain or backbone) and preferably at least one directly or indirectly pendant monovalent acidic group, e.g. sulfonic, phosphinic, or preferably phosphonic or carboxylic, or salt thereof, e.g. alkali metal or ammonium. It is ordinarily desirable that the repeating units constitute at least about 10%, preferably at least about 50%, more preferably at least about 80% up to 95% or 100% by weight of the polymer. Preferably, about 0.02–5%, more preferably about 0.1 to about 2.5% of the cross-linked polymer is employed in the oral compositions of this invention.

According to a preferred embodiment, the required cross-linked polymer is derived from a synthetic anionic polymeric polycarboxylate, many types of which are disclosed in the prior art, for example, as anticalculus agents in U.S. Pat. No. 3,429,963 to Shedlovsky; U.S. Pat. No. 4,152,420 to Gaffar; U.S. Pat. No. 3,956,480 to Dichter et al; U.S. Pat. No. 4,138,477 to Gaffar; and U.S. Pat. No. 4,183,914 to Gaffar et al.

These synthetic anionic polymeric polycarboxylates are often per se employed in the form of their free acids or preferably partially or more preferably fully neutralized water soluble or water swellable (hydratable, gel/-forming) alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether/maleic anhydride (MVE/MA) having a molecular weight (M.W.) of about 30,000 to about 1,000,000. These copolymers are available, for example, as Gantrez e.g. AN 139 (M. W. 500,000), AN 119 (M. W. 250,000); and S-97 Pharmaceutical Grade (M.W. 70,000), of GAF Corporation. Also useful are terpolymers such as 1.0 MA/0.4 MVE/0.1 dodecane, 1.0 MA/0.75 MVE/0.25 decene, 1.0 MA/0.95 MVE/0.05 eicosene or tetradecene, 1.0 MA/0.9 MVE/0.1 tetradecene, 1 MA/1/0.9 MVE/0.1 acrylic acid, vinylpyrrolidone or isobutane.

Other operative polymeric polycarboxylates include those disclosed in U.S. Pat. No. 3,956,480 referred to above, such as the 1:1 copolymers of maleic anhydride with ethyl acrylate, hydroxyethyl methacrylate, N-vinyl-2-pyrollidone, or ethylene, the latter being available, for example, as Monsanto EMA No. 1103, M.W. 10,000 and EMA grade 61, and 1:1 copolymers of acrylic acid with methyl or hydroxyethyl methacrylate, methyl or ethyl acrylate, isobutyl vinyl ether or N-vinyl-2-pyrollidone.

Additional operative polymeric polycarboxylates disclosed in above referred to U.S. Pat. No. 4,138,477 and 4,183,914, include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorosorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers ordinarily contain sufficient carboxylic salt groups for water-solubility.

The synthetic anionic polymeric polycarboxylate component is most often a hydrocarbon with optional halogen and O-containing substituents and linkages as present in, for example, ester, ether and OH groups.

According to another preferred embodiment of this invention, the required cross-linked polymer is derived from a polymer containing repeating units in which one or more phosphonic acid groups are bonded to one or more carbon atoms in the polymer chain. Examples of such poisoners are poly (vinyl phosphonic acid) containing units of the formula:

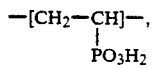
$$-[CH_2-CH]-, \quad\quad\quad I$$
$$\quad\quad\; |$$
$$\quad\quad\; PO_3H_2$$

a copolymer having units of vinyl phosphonic acid of formula I alternating or in random association with units of vinyl phosphonyl fluoride, poly(1-phosphonopropene) with units of the formula:

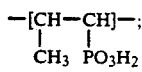
$$-[CH-CH]-; \quad\quad\quad II$$
$$\; | \quad\; |$$
$$CH_3 \; PO_3H_2$$

poly (beta styrene phosphonic acid) containing units of the formula:

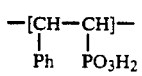
$$-[CH-CH]- \quad\quad\quad III$$
$$\; | \quad\; |$$
$$Ph \; PO_3H_2$$

wherein Ph is phenyl; a copolymer of beta styrene phosphonic acid with vinyl phosphonic acid having the units of Formula III alternating or in random association with units of Formula I above, and poly (alpha styrene phosphonic acid) containing units of the formula:

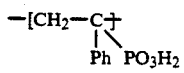
$$-[CH_2-C]- \quad\quad\quad IV$$
$$\quad\;\; | \;\;\backslash$$
$$\quad\;\; Ph \; PO_3H_2$$

These styrene phosphonic acid polymers and their copolymers with other inert ethylenically unsaturated monomers generally have molecular weights in the range of about 2,000 to about 30,000, preferably about 2,500 to about 10,000. Such "inert" monomers are those which do not significantly interfere with the intended function of the cross-linked polymer.

Other phosphonic containing polymers include, for example, phosphonated ethylene having units of the formula.

$$-[(CH_2)_{14}CHPO_3H_2]_n-$$

where n may, for example, be an integer or have a value giving the polymer a molecular weight of about 3,000; sodium poly (1,2 butene-4, 4 -diphosphonate) having units of the formula:

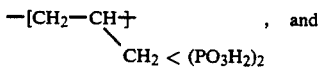
$$-[CH_2-CH]- \quad\quad , \text{ and} \quad\quad VI$$
$$\quad\quad\; \backslash$$
$$\quad\quad\; CH_2 < (PO_3H_2)_2$$

poly allyl bis (phosphonoethyl amine) having units of the formula:

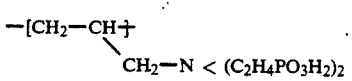
$$-[CH_2-CH]- \quad\quad\quad VII$$
$$\quad\quad\; \backslash$$
$$\quad\quad\; CH_2-N < (C_2H_4PO_3H_2)_2$$

Still other phosphonated polymers include, for example, poly (allyl phosphono acetate), phosphonated polymethacrylate, etc. and the geminal diphosphonate polymers disclosed in EP Publication 0321233.

As illustrative of polymers containing phosphinic acid and/or sulfonic acid groups, there may be mentioned polymers and copolymers containing units or moieties derived from the polymerization of vinyl or allyl phosphinic and/or sulfonic acids. Mixtures of these monomers may be employed, and copolymers thereof with one or more inert polymerizable ethylenically unsaturated monomers such as those described above with respect to the operative synthetic anionic polymeric polycarboxylates. As will be noted, in these and other cross-linkable polymers for use herein, usually only one acidic group is bonded to any given carbon or other atom in the polymer backbone or branch thereon. Polysiloxanes containing or modified to contain pendant acidic groups may also be employed herein. Also effective are ionomers containing or modified to contain acidic groups. Ionomers are described on Pages 546-573 of the Kirk-Othmer Encyclopedia of Chemical Technology, third edition Supplement volume, John Wiley and Sons, Inc. copyright 1984, which description is incorporated herein by reference. Also effective, provided they contain or are modified to contain acidic groups, are polyesters, polyurethanes and synthetic and natural polyamides including proteins and proteinaceous materials such as collagen, poly (arginine) and other polymerized amino acids.

The cross-linkable polymers and copolymers described above can contain moieties in the chain or backbone derived from polymerizable ethylenically unsaturated monomers in addition to and different from the described acidic group-containing monomeric moieties. Polymerization is conducted in known manner, often in the presence of an initiator, and preferably by slurry polymerization in a solvent medium in which the monomers but not the polymer products are soluble or readily dispersible.

For purposes of this invention, the above-described polymers must be cross-linked to be linearly viscoelastic. The polymers are lightly cross-linked so that they swell and form gels, strong three-dimensional networks in aqueous systems. Excessive cross-linking leading to hard, irreversible polymers is to be avoided. The amount of cross-linking agent can vary from about 0.01 to about 30 wt. % of the total, cross-linked polymer, preferably about 2 to about 20 wt. %, more preferably about 3 to about 15 wt. %.

According to a preferred embodiment, cross-linking is carried out concurrently during polymerization of the monomeric components of the polisher by including therein the requisite amount of cross-linking agent. In this embodiment, the cross-linking agents are typically hydrocarbons of at least 4, preferably at least 5, up to about 30, carbon atoms containing 2, less preferably 3 or more, polymerizable activated ethylenically unsaturated groups preferably in non-conjugated, terminal relationship. They can contain optional halogen and/or oxygen-containing substituents and linkages such as ester, ether and OH groups. Examples of such cross-linking agents include 1, 7octadiene, 1, 9-decadiene, 1, 5-hexadiene, divinyl glycol, butanediol divinyl ether, N,N'-methylenebisacrylamide, polyethylene glycol diacrylates and dimethacrylates which in each case are derived from polyethylene glycol with a molecular weight of 126 to 85000, trimethylolpropane triacrylate and trimethacrylate, ethylene glycol, propylene glycol, butanediol, hexanediol and dodecanediol diacrylates and dimethacrylates, the diacrylates and dimethacrylates of block copolymers derived from ethylene oxide and propylene oxide, multivalent alcohols (e.g. glycerol, sucrose or pentaerythritol) di- or triesterified with acrylic acid or methacrylic acid, triallylamine, tetraallylethylenediamine, divinylbenzene, diallyl phthalate, polyethylene glycol divinyl ether, trimethylolpropane diallyl ether, polyallyl sucrose and pentaeythritol, and divinylethylene urea and mixtures thereof.

U.S. Pat. No. 5,034,488 to Tazi et al (GAF) discloses a concurrent cross-linking polymerization process as described above in the production of cross-linked copolymers of maleic anhydride and an alkyl vinyl ether such as methyl vinyl ether operative herein as AEA's to enhance the antibacterial activity of NAA's.

According to another embodiment, cross-linking can be achieved after the cross-linkable polymer is formed (postpolymerization) by reaction with amounts of polyfunctional cross-linking agents reactive with corresponding amounts of pendant reactive groups along the polymer chain, e.g. OH, $NH_2$, $CONH_2$ and especially the aforementioned acidic (e.g. carboxylic, phosphonic, phosphinic, sulfonic, etc.) groups in the polymer. Cross-linking agents reactive with the acidic groups usually contain at least about 4 up to about 30 carbon atoms and may include, for example, linear and cyclic polyols such as butane and octadecane diols, polyethylene glycol, glycerol, sucrose and pentaerythritol, and the corresponding polythiols and polyamines such as hexamethylene and octadecane aliamines and the like. Cross-linking agents reactive with other of the aforesaid pendent reactive groups include the corresponding polyfunctional acidic compounds, e.g. containing at least 2 of the foresaid acidic groups such as butane, decane and octadecane dicarboxylic acids. Post-polymerization is usually less preferred since the resulting cross-linked products often tend to be more easily subject to hydrolysis or the like with resulting loss of the desired linearly viscoelastic properties.

It will be understood that for post-polymerization cross-linking of maleic anhydride-containing polymers and copolymers, the anhydride ring must first be opened by hydrolysis to release the free —COOH groups needed for reaction with the cross-linking agent.

The above-described cross-linked polymers enhances the antibacterial antiplaque activity of NAA's in substantially all forms of oral compositions such as paste or gel dentrifrices, liquid dentrifrices (applied professionally) dental tablets and powders, mouthwashes, chewing gum, lozenges and the like, but their thickening or viscoelastic functions are substantially only useful in paste, gel and liquid dentifrices, and in some cases to render mouthwashes slightly more viscous.

According to a further aspect of this invention, an effective anticalculus amount of an anticalculus agent is desirably included in these oral compositions. Linear, molecularly dehydrated (generally water soluble and synthetic) polyphosphates (i.e. hexametaphosphates, tripolyphosphates, pyrophosphates) are preferred anticalculus agents.

U.S. Pat. No. 4,515,772 to Parran et al discloses and claims oral anticalculus compositions containing a fluoride ion source and soluble dialkali metal pyrophosphates alone or admixed with tetraalkali metal pyrophosphates. U.S. Pat. No. 4,627,977 to Gaffar et al, the disclosure of which is incorporated herein, discloses oral compositions containing the aforesaid preferred polyphosphate anticalculus agents in combination with a fluoride and a polymeric polycarboxylate to inhibit enzymatic hydrolysis of the polyphosphate in saliva. Such polycarboxylates, when cross-linked, are operative herein as AEA's The linear molecularly dehydrated polyphosphates are generally employed in the form of their wholly or partially neutralized water soluble or readily water dispersible alkali metal (e.g. sodium or potassium) or ammonium salts, and any mixtures thereof. Representative examples include sodium hexametaphospate, sodium tripolyphosphate, disodium diacid, trisodium monoacid and tetrasodium pyrophosphates, the corresponding potassium salts and the like. Especially desirable are the tetraalkali metal pyrophosphates such as tetrasodium pyrophosphate (TSPP), tetrapotassium pyrophosphate (TKPP) and mixtures thereof, especially mixtures in which TKPP is predominant. These polyphosphate anticalculus agents, when employed in oral compositions of the invention, are present in approximate weight amounts of 0.1 to 7%, typically 0.1 to 3%, usually 2%.

The sources of fluoride ions, or fluoride ion-providing compounds, when employed herein as an inhibitor of enzymatic hydrolysis of polyphosphate anticalculus agents and/or as anti-caries agents are well known. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal, alkaline earth metal salts, for example, sodium fluoride, potassium fluoride, ammonium fluoride, calcium fluoride, a copper fluoride such as cuprous fluoride, zinc fluoride, barium fluoride, sodium fluorosilicate, ammonium fluorosilicate, sodium fluorozirconate, sodium monofluorophosphate, aluminum mono- and difluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluoride-providing compound is dependent to some extent upon the type of compound, its solubility, and the type of oral preparation, but it must be a nontoxic amount, generally about 0.005 to about 3.0% in the preparation. In a dentifrice preparation, e.g. dental gel, toothpaste (including cream), toothpowder, or dental tablet, an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferably about 800 to about 1,500 ppm of fluoride ion. Typically, in the cases of alkali metal fluorides and stannous fluoride, this compound is present in an amount up to about 2% by weight, based on the weight of the preparation, and preferably in the range of about 0.05% to 1%. The compound may be present in an amount of about 0.1–3%, more typically about 0.76% in the form of sodium monofluorophosphate, (MFP) and about 0.005–1%, more typically about 0.243% in the form of sodium fluoride (NaF).

In oral preparations such as mouthwashes, lozenges and chewing gum, the fluoride-providing compound is typically present in an amount sufficient to release up to about 500 ppm, preferably about 25 to about 300 ppm by weight of fluoride ion. Generally, about 0.005 to about 1.0 wt. % of such compound is present.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation. The alcohol may be isopropanol or the like, or usually and preferably ethanol.

The pH of such liquid and other preparations of the invention is generally in the range of from about 4.5 to about 10 and typically from about 5.5 to 9. The pH is preferably in the range of from about 6 to about 8.0. It is noteworthy that the compositions of the invention may be applied orally at a pH below 5 without substantially decalcifying or otherwise damaging dental enamel. The pH can be controlled with acid e.g. citric acid or benzoic acid) or base (.e.g. sodium hydroxide) or buffered (as with sodium citrate, benzoate, carbonate, or bicarbonate, disodium hydrogen phosphate, sodium dihydrogen phosphate, etc.).

In certain other desirable forms of this invention, the oral composition may be substantially solid or pasty in character, such as toothpowder, a dental tablet, a toothpaste, dental gel or cream. The vehicle of such solid or pasty oral preparations generally contains polishing material. Examples of polishing materials are water-insoluble sodium metaphosphate. potassium metaphosphate, tricalcium phosphate, dihydrated calcium phosphate, anhydrous dicalcium phosphate, dihydrated calcium, phosphate, anhydrous pyrophosphate, magnesium orthophosphate, trimagnesium phosphate, calcium carbonate, aluminum silicate, zirconium silicate, silica, bentonite, and mixtures thereof. Other suitable polishing materials include the particulate thermosetting resins described in U.S. Pat. No. 3,070,510 of Dec. 15, 1962 such as melamine-, phenolic-, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 cm.$^2$/gm., silica gel or colloidal silica, and complex amorphous alkali metal alumino-silicate.

When visually clear gels are employed, a polishing agent of colloidal silica, such as those sold under the trademark SYLOID as Syloid 72 and Syloid 74 or under the trademark SANTOCEL as Santocel 100 and alkali metal alumino-silicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner as illustrated by Thorpe's *Dictionary of Applied Chemistry*, Volume 9, 4th Edition, pp. 510–511. The forms of insoluble sodium metaphosphate known as Madrell's salt and Kurrol's salt are further examples of suitable materials. These metaphosphate salts exhibit only a minute solubility in water and therefore are commonly referred to as insoluble metaphosphates (IMP). There is present therein a minor amount of soluble phosphate material as impurities, usually a few percent such as up to about 4% by weight. The amount of soluble phosphate material, which is believed to include a soluble sodium trimetaphosphate in the case of insoluble metaphosphate, should be reduced or eliminated as by washing with water. The insoluble alkali metal metaphosphate is typically employed in powder form of a particle size such that no more than about 1% of the material is larger than about 37 microns.

The polishing material is generally present in the solid or pasty compositions in weight concentrations of about 10% to about 99%. Preferably, it is present in amounts ranging from about 10% to about 75% in toothpaste, and from about 70% to about 99% in toothpowder.

In a toothpaste, the liquid vehicle may comprise water and humectant typically in an amount ranging from about 10% to about 90% by weight of the preparation. Glycerine, propylene glycol, sorbitol, polypropylene glycol and/or polyethylene glycol (e.g. 400–600) exemplify suitable humectants/carriers. Also advantageous are liquid mixtures of water, glycerine and sorbitol. In clear gels where the refractive index is an important consideration, about 3–30 wt. % of water, 0 to 80 wt. % of glycerine, and about 20–80 wt. % of sorbitol is preferably employed.

It will be understood that other conventional thickeners (binding, gelling agents) may be included in these dentifrice compositions, usually in amounts ranging from about 0.1 to about 4 parts by weight of the defined cross-linked polymeric thickener. Examples of such other thickeners include xanthan gum, hydroxyethyl cellulose and water-soluble salts of cellulose ether such as sodium carboxymethyl cellulose and sodium carboxymethyl hydroxyethyl cellulose. Natural gums such as carrageenan (Irish moss, Viscarin), gum karaya, gum arabic, and gum tragacanth can also be used. Colloidal magnesium aluminum silicate, Veegum or finely divided silica can be used as part of the thickening agent system. Preferred thickening agents include xanthan gum, carrageenan, sodium carboxymethyl cellulose, sodium carboxymethyl hydroxyethyl cellulose and hydroxyethyl cellulose, preferably in proportions of about 0.4 to about 3 parts per part of the cross-linked polymeric thickener. Also useful is synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners include starch, polyvinylpyrrolidone, hydroxybutyl methyl cellulose, hydroxypropyl methyl cellulose, alginates, gum ghatti, locust bean gum, pectins, and tamarind gum and the like.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste, cream or gel will usually be in a collapsible tube, typically aluminum, lined lead or plastic, or other squeeze, pump or pressured dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts or higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2 dihydroxy propane sulfonates, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Various other materials may be incorporated in the oral preparations of this invention such as whitening agents, preservatives, silicones, chlorophyll compounds, other anticalculus agents, and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, APM (aspartyl phenylalanine methyl ester), saccharine and the like. Suitably, flavor and sweetening agents may together comprise from about 0.1% to 5$ more of the preparation.

In the preferred practice of this invention an oral composition according to this invention such as a mouthwash or dentifrice is applied regularly to the oral cavity as by "swishing" or brushing dental surfaces, such as every second or third day or preferably from 1 to 3 times daily, at a pH of about 4.5 to about 10, generally about 5.5 to about 9, preferably about 6 to 8, for at least 2 weeks up to 8 weeks or more up to lifetime. The composition is typically removed by rinsing with water after each application.

The compositions of this invention can be incorporated in lozenges, or in chewing gum or other products, e.g. by stirring into a warm gum base or coating the outer surface of a gum base, illustrative of which may be mentioned jelutone, rubber latex, vinylite resins, etc., desirably with conventional plasticizers or softeners, sugar or other sweeteners or carbohydrates such as glucose, sorbitol and the like.

The vehicle or carrier in a tablet or lozenge is a noncariogenic solid water soluble polyhydric alcohol (polyol) such as mannitol, xylitol, sorbitol, maltitol, a hydrogenated starch hydrolysate, Lycasin, hydrogenated glucose, hydrogenated disaccharides, and hydrogenated polysaccharides, in an amount of about 90–98% by weight of the total composition. Solid salt such as sodium bicarbonate, sodium chloride, potassium bicarbonate or potassium chloride may totally or partially replace the polyol carrier.

Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and carbowax.

Lozenge formulations contain about 2% gum as barrier agent to provide a shiny surface as opposed to a tablet which has a smooth finish. Suitable non-cariogenic gums include Kapa carrageenan, carboxymethyl cellulose, hydroxyethyl cellulose, Gantrez, and the like.

The lozenge or tablet may optionally be coated with a coating material such as waxes, shellac, carboxymethyl cellulose, polyethylene/maleic anhydride copolymer or Kappa-carrageenan to further increase the time it take the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

The following Examples A–F illustrate the preparation of operative synthetic cross-linked polymers and their properties. All parts, amounts and proportions referred to herein and in the appended claims are by weight, and temperatures are in degrees C unless otherwise indicated.

| Post Polymerization Cross-Linking | | |
| --- | --- | --- |
| | Example A | Example B |
| PVM/MA* | 0.33330 Moles | 0.33001 Moles |
| PEG 600** | 0.00166 " | 0.00249 " |
| MEK*** | 6.6 | 6.6 |

*Gantrez AN139, vinylmethyl ether/maleic anhydride 1/1 copolymer M.W. 500,000 (GAF Corp.).
**Polyethylene glycol, M.W 600 (13–14 E.O.)
***Methyl ethyl ketone The PVM/MA copolymer is dissolved in the MEK (b.pt. 80° C.) yielding a 10 wt. % solution, in a stirred 1 liter resin kettle. The PEG is then added and the liquor refluxed for about 4 hours. At least 400 ml. of MEK are collected by distillation through a cold water condenser. A pink viscous syrup results which is poured at 50°–60° C. into a large evaporating dish and further devolatized under vacuum at 60°–70° C. overnight.

Through the starting PVM/MA copolymer is both ketone-soluble and water-soluble to a high degree, the products of both Examples 1 and 2 are pink, very hard solids, only slightly soluble in ketones, and insoluble but rapidly swelling in water to form gels. I.R. spectrum analyses show that the staring polymer has no free —COOH groups but both products show strong —COOH peaks resulting from ring opening and ester cross-links, indicative of an Example A product containing about 0.5 mole % or about 2 wt. % of PEG cross-linkages and an Example B product containing about 0.75 mole % or about 3 wt. % of PEG cross-linkages.

Concurrent Cross-Linking Polymerization

Example C

In a one liter pressure reactor are charged the following: 404.4 parts cyclohexane, 269.6 parts ethyl acetate, and 6 parts 1,7 octadiene. 0.3 Parts of the initiator t-butylperoxypivilate are added at 58° C. in three increments of 0.1 part each at times: 0, 60, and 120 minutes from the first addition. Seventy-five parts of molten maleic anhydride and 49.0 parts of methyl vinyl ether are mixed together and gradually added to the reaction vessel at 58° C. and 65 psi (natural pressure of the system) over a 2 hour period of time. The reaction mixture is then held at 58° C. for two hours after the last addition of initiator. The presence of maleic anhydride is followed by testing with triphenyl phosphene. The product precipitates out of solution (slurry polymerization). After the reaction is complete, the product is cooled to room temperature, filtered and dried in a vacuum oven. It is a 1:1 cross-linked copolymer and methyl vinyl ether and maleic anhydride (PVM/MA) containing about 4.6 wt. % of the octadiene cross-linking agent.

Example D

The procedure of Example C is repeated using 5 parts of 1,9-decadiene instead of the 6 parts of 1,7-octadiene. The product, in the form of a white powder, has the following viscosity specifications in varying concentrations in aqueous solution at pH 7 and 25° C. by Brookfield RVT, Spindle TC at 10 RPM:

TABLE 1

| Concentration | Viscosity |
| --- | --- |
| 0.25% | 30,800 cps |
| 0.50% | 63,500 cps |
| 1.00% | 90,000 cps |

An 0.5% aqueous solution of this product, pH adjusted to 7, has the following viscosity properties when measured with a Brookfield Model RVT, Spindle TC, at varying RPM's:

TABLE 2

| RPM | Viscosity |
| --- | --- |
| 1 | 376 × 10³ cps |
| 2.5 | 180 × 10³ cps |
| 5 | 105 × 10³ cps |
| 10 | 59 × 10³ cps |

These results show that even at very low concentrations this cross-linked PVM/MA copolymer yields highly viscous solutions.

The following yield points of varying concentrations of this polymer in aqueous solution at pH 7 are obtained using the Haake Rotoviscometer RV12 with MV IP sensor system and shear rates varied from 0 to 10 sec$^{-1}$:

TABLE 3

| Concentration | Yield Point (Pascals) |
| --- | --- |
| 0.125 | 37 |
| 0.250 | 64 |
| 0.500 | 180 |

These high-yield points, corresponding to the amount of shear stress needed to initiate flow, indicate gel network formation enabling permanent stabilization of suspensions of particles such as insoluble polishing materials in dentrifrices compositions.

Example E

One percent aqueous solutions of cross-linked PVM/MA copolymer containing from 0.01% to 10% of 1,7-octadiene cross-linking agent, prepared as described in Example C, are shaken overnight in order to hydrolyze the maleic anhydride ring and then neutralized with NaOH to fully ionize the carboxyl groups. The results listed in the following table indicate that solutions containing more than 2.5%, i.e. at least about 3% of cross-linking agent gel whereas solutions containing up to 2.5% cross-linking agent do not gel.

TABLE 4

| Wt. % Cross-Linking Agent | Gelling Results |
|---|---|
| 0.1 | No gel |
| 0.5 | No gel |
| 1.0 | No gel |
| 2.5 | No gel |
| 5.0 | Gelled |
| 7.5 | Gelled |
| 10.0 | Gelled |

Example F

Optional Hydrolysis Procedure

To a 2 liter kettle fitted with a mechanical agitator and a reflux column add 962 grams of deionized water and 28 grams of a 10% aqueous sodium hydroxide solution. Heat to 65° C. and add 10 grams of the product of Example D with stirring. The system becomes clear within 2 hours and has a pH of about 7. The resultant gel has a solids content of 1%.

The following examples are only illustrative of the compositions of this invention. Typically, the cross-linked polymer or copolymer is hydrolyzed in water for 2 to 3 days at an appropriate solids concentration varying from about 5 to 10% polymer content, neutralized to pH 7, the mixture dispersed in the humectant system, and the resulting dispersion mixed with the other dentifrice ingredients at a pH of about 7.

Following known and science-recognized procedures, hydroxyapatite (HA), the mineral phase of dental enamel, was used as an in vitro experimental model for human teeth to evaluate the effect of the cross-linked polymer on the delivery and retention of triclosan to tooth surfaces. HA disk was coated with saliva to form a salivary pellicle on the disk. The disk was used instead of HA powder which has a very high surface area nd does not simulate in vivo surface to volume ratios. Dentifrice liquid phase solution as in Table 5 below containing triclosan with an without the polymer was made with all the components of dentifrice except abrasive and used for the uptake study. The XL Gantrez corresponds to the product of Example C above, namely, maleic anhydride and methyl vinyl ether concurrently copolymerized with 1,7 octadiene cross-linking agent.

TABLE 5

| Composition of Dentifrice Liquid Phase Solution | |
|---|---|
| Ingredients | Parts |
| Sorbitol (70% aqueous) | 30.0 |
| Glycerol | 9.5 |
| Propylene Glycol | 0.5 |
| Sodium Lauryl Sulfate | 2.0 |
| Polymer | X |
| Flavor Oil | 0.95 |
| Triclosan | 0.3 |
| Water | 55.257 | pH was adjusted to 6.5 by adding 50% NaOH solution.

Results are as follows:

TABLE 6

| Example | % Polymer X | Triclosan Uptake ug/Disk; n = 3 |
|---|---|---|
| 1 | 0.1 XL Gantrez | 152.5 +/− 5.1 |
| 2 | 0.3 XL Gantrez | 167.7 +/− 6.4 |
| 3 | 0.5 XL Gantrez | 139.0 +/− 6.2 |
| 4 | 0.75 XL Gantrez | 180.8 +/− 7.6 |
| G | None | 33.0 +/− 4.0 |
| H | 2% Gantrez S-97 | 90.5 +/− 5.1 |

The results in Table 6 show that 0.1% Gantrez cross-linked with 5% of 1,7-Octadiene enhances the uptake of triclosan from dentifrice liquid phase solution to saliva coated HA disk by 4.6 and 1.68 fold compared to the negative control (no polymer) and 2% Gantrez, respectively. The results further show that the uptake of triclosan to saliva coated HA disk is enhanced with increased concentration of cross-linked Gantrez.

The above HA/triclosan uptake procedure was followed with the following liquid phase dentifrice solution using Gantrez-based terpolymers, shown in Table 7, similarly cross-linked with 5% of 1,7-octadiene.

TABLE 7

| Composition of Dentifrice Liquid Phase Solution | |
|---|---|
| Ingredients | Parts |
| Sorbitol (70% aqueous) | 10.0 |
| Glycerol | 20.0 |
| Sodium Lauryl Sulfate | 2.5 |
| Polymer | X |
| MFP | 0.8 |
| Flavor Oil | 0.3 |
| Triclosan | 0.3 |
| Water | 65.15 | pH was adjusted to 6.5 by adding 50% NaOH solution.

Results are as follows:

TABLE 8

| Example | % Polymer X | Triclosan Uptake ug/Disk; n = 3 |
|---|---|---|
| 5 | 0.3 XL MA/MVE/AA 1/0.9/0.1 | 120.0 +/− 8.0 |
| 6 | 0.3 XL MA/MVE/IB 1/0.9/0.1 | 122.2 +/− 0.2 |
| 7 | 0.3 XL MA/MVE/VP 1/0.9/0.1 | 109.0 +/− 8.0 |
| I | None | 33.0 +/− 4.0 |
| J | 2% Gantrez S-97 | 95.5 +/− 5.1 |

MA: Maleic Anhydride; MVE: Methyl vinyl Ether; AA: Acrylic Acid; IB: Isobutylene; VP: Vinyl pyrrolidone. 0.3% Triclosan was used in the dentifrice liquid phase solution as shown in Table 7.

The results shown in Table 8 indicate the cross-linked terpolymers to be also unexpectedly and substantially improved and effective for controlling plaque.

Following are further formulations illustrative of oral compositions according to this invention, in which XL polymer can be any of the cross-linked polymers disclosed in Examples A-F, 1-7, and elsewhere herein. All formulations exhibit unexpectedly improved plaque control.

| Dentifrice Compositions | | | | |
|---|---|---|---|---|
| | Example (Parts by Weight) | | | |
| Ingredients | 8 | 9 | 10 | 11 |
| Sorbitol (70% aqueous) | 20 | | 20.0 | 20.0 |
| Glycerol | 10.0 | 22.0 | 10.0 | 10.0 |
| Propylene Glycol | 0.5 | 0.5 | 0.5 | |
| Iota Carrageenan | 0.75 | 0.75 | 0.75 | 0.75 |
| Na Saccharin | 0.3 | 0.3 | 0.3 | 0.3 |
| MFP[1] | 0.76 | 0.76 | 0.76 | 0.76 |
| TiO$_2$ | 0.5 | 0.5 | 0.5 | 0.5 |
| XL Polymer | 0.3 | 0.3 | 0.3 | 0.3 |
| Zeodent 113[2] | 20.0 | | 20.0 | 20.0 |
| Sylodent 15[3] | 3.0 | | 3.0 | 3.0 |
| Alumina[4] Baco Af230 | | 48.0 | | |
| Flavor Oil | 0.95 | 0.95 | 0.95 | 0.95 |
| SLS[5] | 2.0 | 2.0 | 2.0 | 2.0 |
| Triclosan | 0.3 | 0.3 | 0.3 | 0.3 |
| TSPP[6] | | | 2.0 | |
| Water Q.S. to | 100.0 | 100.0 | 100.0 | 100.0 |

| Mouthwashes | |
|---|---|
| | Example |
| | 12    13 |

-continued

| Ingredients | Parts | Parts |
|---|---|---|
| TSPP | 2.00 | — |
| XL Polymer | 0.1 | 0.1 |
| Glycerine | 10.00 | 10.00 |
| Propylene Glycol | 5.00 | 5.00 |
| Sodium Fluoride | 0.05 | — |
| Pluronic F108 (Polyoxyethylene/Polyoxypropylene Block Copolymer) | 1.0 | 1.0 |
| Triclosan | 0.10 | 0.10 |
| Flavor | 0.40 | 0.40 |
| Water Q.S. to | −100.00 | −100.00 |

Example 14
Lozenge

| | |
|---|---|
| 75–80% | Sugar |
| 1–20% | Corn Syrup |
| 0.1–1% | Flavor Oil |
| 2% | TSPP |
| 0.1–0.3% | XL Polymer |
| 0.01–0.1% | MFP |
| 0.01–0.1% | Triclosan |
| 1–5% | Magnesium Stearate Lubricant |
| 0.01–0.2% | Water |

Chewing Gum

| | Example (Parts by Weight) | |
|---|---|---|
| Ingredients | 15 | 16 |
| Gum Base | 25.0 | 30.0 |
| Sorbitol | 17.0 | 53.0 |
| Triclosan | 0.1–0.5 | 0.1–0.5 |
| MFP | 0.1 | 0.1 |
| XL Polymer | 0.1–0.3 | 0.1–0.3 |
| Flavor Oil | 0.1–1.0 | 0.1–1.0 |
| TSPP | 2.0 | |
| Water Q.S. to | −100.0 | −100.0 |

[1] Sodium monofluorophosphate (replaceable by 0.243 NaF)
[2] Silica polishing agent
[3] Slicia thickener
[4] Polishing agent
[5] Sodium lauryl sulfate
[6] Tetrasodium pyrophosphate This invention has been described with respect to certain preferred embodiments and it will be understood that modifications and variations thereof obvious to those skilled in the art are to be included within the spirit and purview of this application and the scope of the appended claims.

We claim:

1. An oral composition comprising in an orally acceptable vehicle an effective antiplaque amount of a substantially water insoluble noncationic antibacterial agent and an antibacterial-enhancing agent in an amount effective to enhance delivery of said antibacterial agent to, and the retention thereof on, oral surfaces, said antibacterial-enhancing agent comprising a synthetic cross-linked polymer having in a 1 wt.% aqueous solution an elastic or storage modulus $G'$ and a viscous or loss modulus $G'$ substantially independent of frequency in an applied frequency range of 0.1 to 100 radiants/sec., a $G'$ minimum value of 5,000 dynes/sq. cm which varies less than 1 order of magnitude of its original value, and a ratio of $G'/G'$ ranging from more than 0.05 to less than 1.

2. A composition according to claim 1 wherein said polymer has a molecular weight of about 1,000 to about 5,000,000.

3. A composition according to claim 2 wherein said polymer contains a plurality of carboxylic, phosphonic, phosphinic or sulfonic acid or acid salt groups or mixtures thereof.

4. A composition according to claim 3 wherein said polymer is made with a cross-linking agent containing at least two ethylenically unsaturated groups or at least two groups reactive with pendent reactive groups along the polymer chain.

5. A composition according to claim 4 wherein said polymer comprises a co-polymer of maleic acid or anhydride with another ethylenically unsaturated monomer.

6. A composition according to claim 5 wherein said other monomer comprises methyl vinyl ether.

7. A composition according to claim 6 wherein said copolymer is made with 1,7-octadiene, 1,9-decadiene, or polyethylene glycol as cross-linking agent.

8. A composition according to any of claims 1 to 7 wherein said antibacterial agent comprises a halogenated diphenyl ether, a halogenated salicylanilide, a benzoic ester, a halogenated carbanilide or a phenolic compound or any mixture thereof.

9. A composition according to any of claims 1 to 7 wherein said antibacterial agent comprises a halogenated diphenyl ether.

10. A composition according to claim 8 containing about 0.01 to about 5% of said antibacterial agent.

11. A composition according to claim 10 wherein said antibacterial agent comprises a halogenated diphenyl ether.

12. A composition according to claim 11 wherein said halogenated diphenyl ether comprises triclosan.

13. A composition according to any of claims 1 to 7 further containing an effective anticalculus amount of material comprising at least one linear molecularly dehydrated polyphosphate salt as anticalculus agent.

14. A composition according to claim 13 wherein said material comprises tetrasodium pyrophosphate, tetrapotassium pyrophosphate or a mixture thereof.

15. A composition according to claim 12 wherein said material comprises tetrasodium pyrophosphate, tetrapotassium pyrophosphate or a mixture thereof.

16. A composition according to anyone of claims 1 to 7 further containing an amount of a fluoride ion source sufficient to supply about 25 ppm to about 5,000 ppm of fluoride ions.

17. A composition according to claim 12 further containing an amount of a fluoride ion source sufficient to supply about 25 ppm to about 5,000 ppm of fluoride ions.

18. A composition according to claim 15 further containing an amount of a fluoride ion source sufficient to supply about 25 ppm to about 5,000 ppm of fluoride ions.

19. A composition according to anyone of claims 1 to 7 containing an amount of said cross-linked polymer effective to render the composition linearly viscoelastic.

20. A composition according to claim 12 containing an amount of said cross-linked polymer effective to render the composition linearly viscoelastic.

21. A composition according to claim 15 containing an amount of said cross-linked polymer effective to render the composition linearly viscoelastic.

22. A composition according to claim 18 containing an amount of said cross-linked polymer effective to render the composition linearly viscoelastic.

23. A composition according to any one of claims 1 to 7 in the form of a dentifrice containing a dentally acceptable polishing agent and a vehicle comprising water and humectant.

24. A composition according to claim 12 in the form of a dentifrice containing a dentally acceptable polishing agent and a vehicle comprising water and humectant.

25. A composition according to claim 15 in the form of a dentifrice containing a dentally acceptable polishing agent and a vehicle comprising water and humectant.

26. A composition according to claim 18 in the form of a dentifrice containing a dentally acceptable polishing agent and a vehicle comprising water and humectant.

27. A composition according to claim 22 in the form of a dentifrice containing a dentally acceptable polishing agent and a vehicle comprising water and humectant.

28. A method of promoting oral hygiene comprising applying to dental surface an effective amount of a composition as defined in any one of claims 1 to 7.

29. A method of promoting oral hygiene comprising applying to dental surface an effective amount of a composition as defined in claim 12.

30. A method of promoting oral hygiene comprising applying to dental surface an effective amount of a composition as defined in claim 15.

31. A method of promoting oral hygiene comprising applying to dental surface an effective amount of a composition as defined in claim 18.

32. A method of promoting oral hygiene comprising applying to dental surface an effective amount of a composition as defined in claim 22.

33. A method or promoting oral hygiene comprising applying to dental surface an effective amount of a composition as defined in claim 27.

* * * * *